United States Patent
Kolbe et al.

(10) Patent No.: US 8,343,465 B2
(45) Date of Patent: Jan. 1, 2013

(54) COOLING COSMETIC OR DERMATOLOGICAL PREPARATIONS COMPRISING (1R,2S,5R)-2-ISOPROPYL-5-METHYL-N-(2-(PYRIDIN-2-YL)ETHYL)-CYCLOHEXANE CARBOXAMIDE AND/OR (1R,2S,5R)-N-(4-CYANOMETHYL-PHENYL)-2-ISOPROPYL-5-METHYLCYCLOHEXANE CARBOXAMIDE FOR REDUCING SKIN REDDENING

(75) Inventors: Ludger Kolbe, Dohren (DE); Julia Eckert, Hamburg (DE); Gitta Neufang, Hamburg (DE); Stefanie Knaupmeier, Hamburg (DE)

(73) Assignee: Beiersdorf AG, Hamburg (DE)

( * ) Notice: Subject to any disclaimer, the term of this patent is extended or adjusted under 35 U.S.C. 154(b) by 516 days.

(21) Appl. No.: 12/402,997

(22) Filed: Mar. 12, 2009

(65) Prior Publication Data
US 2009/0311206 A1 Dec. 17, 2009

(30) Foreign Application Priority Data
Mar. 20, 2008 (DE) .......................... 10 2008 015 426

(51) Int. Cl.
| | |
|---|---|
| A01N 43/08 | (2006.01) |
| A01N 37/12 | (2006.01) |
| A01N 37/44 | (2006.01) |
| A01N 43/36 | (2006.01) |
| A61K 31/34 | (2006.01) |
| A61K 31/24 | (2006.01) |
| A61K 8/19 | (2006.01) |
| A61K 9/00 | (2006.01) |
| C07D 307/00 | (2006.01) |
| C07C 205/00 | (2006.01) |
| C07C 229/00 | (2006.01) |

(52) U.S. Cl. ............ 424/59; 424/73; 514/423; 514/473; 514/541; 549/321; 560/125

(58) Field of Classification Search .................... 424/59, 424/73; 514/423, 541, 473; 549/321; 560/125
See application file for complete search history.

(56) References Cited

U.S. PATENT DOCUMENTS

| | | | |
|---|---|---|---|
| 4,153,679 A * | 5/1979 | Rowsell et al. ................. 424/45 |
| 5,451,404 A | 9/1995 | Furman | |
| 6,642,233 B1 | 11/2003 | Ducoux et al. | |
| 6,951,940 B2 | 10/2005 | Ducoux et al. | |
| 7,414,152 B2 | 8/2008 | Galopin et al. | |
| 2003/0235545 A1 | 12/2003 | Guenin et al. | |
| 2004/0175346 A1 | 9/2004 | Guenin et al. | |
| 2004/0180013 A1 | 9/2004 | Mattai et al. | |
| 2005/0187211 A1 | 8/2005 | Wei | |
| 2006/0276667 A1 | 12/2006 | Galopin et al. | |
| 2007/0280892 A1 | 12/2007 | Kindel et al. | |
| 2008/0124282 A1 | 5/2008 | Emmerling et al. | |
| 2008/0227857 A1* | 9/2008 | Wei .............................. 514/473 |
| 2008/0267889 A1* | 10/2008 | Cernasov et al. ............... 424/47 |

FOREIGN PATENT DOCUMENTS

| | | |
|---|---|---|
| GB | 1 422 998 | 1/1976 |
| WO | 93/23005 A1 | 4/1993 |
| WO | 2005/049553 A1 | 6/2005 |
| WO | 2006/128622 A2 | 12/2006 |
| WO | 2007/019719 A1 | 2/2007 |

OTHER PUBLICATIONS

U.S. Appl. No. 12/402,985, filed Mar. 12, 2009.
U.S. Appl. No. 12/403,011, filed Mar. 12, 2009.

* cited by examiner

*Primary Examiner* — Mina Haghighatian
*Assistant Examiner* — Luke Karpinski
(74) *Attorney, Agent, or Firm* — Abel Law Group, LLP

(57) ABSTRACT

A topical cosmetic and dermatological preparation for reducing skin reddening which comprises (1R,2S,5R)-2-isopropyl-5-methyl-N-(2-(pyridin-2-yl)ethyl)-cyclohexane carboxamide and/or (1R,2S,5R)—N-(4-cyanomethyl-phenyl)-2-isopropyl-5-methylcyclohexane carboxamide.

20 Claims, No Drawings

COOLING COSMETIC OR DERMATOLOGICAL PREPARATIONS COMPRISING (1R,2S,5R)-2-ISOPROPYL-5-METHYL-N-(2-(PYRIDIN-2-YL)ETHYL)-CYCLOHEXANE CARBOXAMIDE AND/OR (1R,2S,5R)-N-(4-CYANOMETHYL-PHENYL)-2-ISOPROPYL-5-METHYLCYCLOHEXANE CARBOXAMIDE FOR REDUCING SKIN REDDENING

CROSS-REFERENCE TO RELATED APPLICATIONS

The present application claims priority under 35 U.S.C. §119 of German Patent Application No. 10 2008 015 426.1, filed Mar. 20, 2008, the entire disclosure of which is expressly incorporated by reference herein.

BACKGROUND OF THE INVENTION

1. Field of the Invention

The present invention relates to cooling cosmetic and dermatological preparations, in particular skin care cosmetic and dermatological preparations.

2. Discussion of Background Information

The present invention relates to cooling cosmetic and dermatological preparations which are capable of reducing skin reddening after shaving, in particular skin care cosmetic and dermatological preparations.

Erythema is the term used to describe a reddening of the skin visible to the naked eye. It is caused by an increased local blood flow (hyperemia) of the cutaneous tissue, for example, within the scope of an inflammation. Erythmatous cutaneous manifestations can occur in particular due to the mechanical stress during shaving.

Erythmatous cutaneous manifestations also occur as accompanying symptoms with certain skin diseases or irregularities. For example, the typical skin rash with the appearance of acne is more or less severely reddened.

It would be advantageous to be able to overcome the disadvantages of the prior art. In particular, it would be desirable to provide active substances and preparations containing such active substances for the cosmetic and dermatological treatment and/or prophylaxis of erythmatous, inflammatory, allergic and/or autoimmune reactive manifestations, in particular dermatoses, as well as of the manifestation of "stinging".

There have hitherto been various cooling substances that evoke a pleasant feeling of freshness on the skin. For example, menthol is used in order to cause a feeling of freshness in after shave formulations. However, menthol has properties irritating to the mucous membranes and can cause further skin irritations, which leads to a burning of the skin. Furthermore, menthol has a strong inherent odor and can lead to intolerances in the eye region.

Accordingly, it would also be advantageous to be able to remedy the problems of the prior art and to provide preparations which reduce erythemas, are simple to produce, do not have an irritating effect on the skin or mucous membranes, have a neutral odor and additionally have a cooling effect when used correctly.

SUMMARY OF THE INVENTION

The present invention provides a topical cosmetic and dermatological preparation for reducing skin reddening. The preparation comprises (i) (1R,2S,5R)-2-isopropyl-5-methyl-N-(2-(pyridin-2-yl)ethyl)cyclohexane carboxamide and/or (ii) (1R,2S,5R)-N-(4-cyanomethyl-phenyl)-2-isopropyl-5-methylcyclohexane carboxamide.

In one aspect, the preparation may further comprise 2-isopropyl-5-methylcyclohexane carbonylamido propionic acid methyl ester, for example, in a total concentration of from about 0.001% to about 10% by weight, e.g., from about 0.01% to about 1% by weight, based on a total weight of the preparation.

In another aspect, the preparation of the present invention may comprise a total of from about 0.001% to about 10% by weight of (i) and/or (ii), based on the total weight of the preparation. For example, the preparation may comprise at least about 0.01%, e.g., at least about 0.05% by weight and/or not more than about 1% by weight of (i) and/or (ii).

In a still further aspect, the preparation of the present invention may further comprise one or more antioxidants and/or one or more vitamins and/or one or more sunscreen agents and/or one or more antiperspirants and/or one or more deodorants.

In another aspect, the preparation may be present as an emulsion and/or may be present as deodorant formulation for reducing skin reddening.

The present invention also provides a topical cosmetic and dermatological preparation for reducing skin reddening that comprises a total of from about 0.01% to about 1% by weight of (i) (1R,2S,5R)-2-isopropyl-5-methyl-N-(2-(pyridin-2-yl) ethyl)-cyclohexane carboxamide and/or (ii) (1R,2S,5R)-N-(4-cyanomethyl-phenyl)-2-isopropyl-5-methylcyclohexane carboxamide in combination with from about 0.01% to about 1% by weight of 2-isopropyl-5-methylcyclohexane carbonylamido propionic acid methyl ester.

The present invention also provides a method of reducing skin reddening after shaving. The method comprises applying to shaved skin the preparation of the present invention as set forth above (including the various aspects thereof).

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description making apparent to those skilled in the art how the several forms of the present invention may be embodied in practice. Unless stated otherwise, all amounts, fractions and percentages given are based on the weight and the total amount or on the total weight of the preparations.

It has surprisingly been found that the following compounds have a cooling and anti-inflammatory effect that reduces reddening:

(1R,2S,5R)-2-isopropyl-5-methyl-N-(2-(pyridin-2-yl) ethyl)-cyclohexane carboxamide

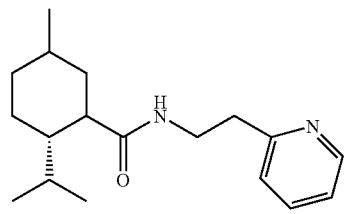 [SMILES: CC1CC[C@@H](C(C)C)C(C(=O)NCCc2ccccn2)C1]

(1R,2S,5R)-N-(4-cyanomethyl-phenyl)-2-isopropyl-5-methylcyclohexane carboxamide

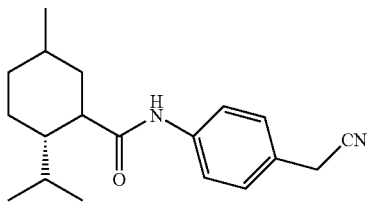 [SMILES: CC1CC[C@@H](C(C)C)C(C(=O)Nc2ccc(CC#N)cc2)C1]

2-isopropyl-5-methylcyclohexane-carbonylamido propionic acid methyl ester

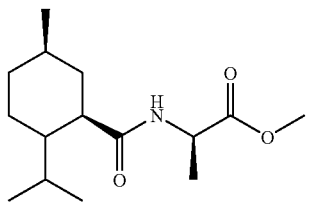 [SMILES: COC(=O)[C@@H](C)NC(=O)[C@@H]1C[C@H](C)CCC1C(C)C]

These cooling substances which are capable of reducing reddening can be used alone or in combination with other cooling substances.

Non-limiting examples of other cooling substances include menthol, menthoxypropane diol (Cooling Agent 10), menthone, ethyl menthane carboxamido acetate (WS-5), isopulegol (Coolact P), menthanediol (Coolact 38D), N,2,3-trimethyl-2-isopropylbutanamide (WS-23), ethyl menthane carboxamide (WS-3), menthone glycerine acetal (Frescolat MGA), and mono-menthyl succinate (Physcool).

There has been no lack of attempts to reduce skin reddening after shaving and to prevent razor burn. However, it was surprising and not foreseeable to one skilled in the art that topical cosmetic or dermatological preparations for reducing skin reddening after shaving which comprise (1R,2S,5R)-2-isopropyl-5-methyl-N-(2-(pyridin-2-yl)ethyl)-cyclohexane carboxamide and/or (1R,2S,5R)-N-(4-cyanomethyl-phenyl)-2-isopropyl-5-methylcyclohexane carboxamide eliminate the disadvantages of the prior art.

The preparations of the present invention are simple to formulate and do not place any great demands on the production processes.

The production of an emulsion and in particular, an O/W emulsion is preferred. To this end, the cooling substances may, for example, be predissolved in one or more alcohols (in particular, polyols) and added to the emulsion at about 40° C. before cooling to room temperature.

The invention also comprises the use of (1R,2S,5R)-2-isopropyl-5-methyl-N-(2-(pyridin-2-yl)ethyl)-cyclohexane carboxamide and/or (1R,2S,5R)-N-(4-cyanomethyl-phenyl)-2-isopropyl-5-methylcyclohexane carboxamide in after shave formulations for reducing skin reddening and the use of (1R,2S,5R)-2-isopropyl-5-methyl-N-(2-(pyridin-2-yl)ethyl)-cyclohexane carboxamide and/or (1R,2S,5R)-N-(4-cyanomethyl-phenyl)-2-isopropyl-5-methylcyclohexane carboxamide in deodorant formulations for reducing skin reddening. It is preferred for the corresponding cosmetic and dermatological preparations to additionally comprise 2-isopropyl-5-methyl cyclohexane-carbonylamido propionic acid methyl ester. It is preferred for the preparations of the present invention to comprise from about 0.001% to about 10% by weight, particularly preferably from about 0.01% to about 1% by weight (for example, not less than about 0.05% by weight, or not less than about 0.1% by weight) of (1R,2S,5R)-2-isopropyl-5-methyl-N-(2-(pyridin-2-yl)ethyl)-cyclohexane carboxamide and/or (1R,2S,5R)-N-(4-cyanomethyl-phenyl)-2-isopropyl-5-methyl-cyclohexane carboxamide, based on the total weight of the preparations. It is also preferred for the preparations of the present invention to additionally comprise 2-isopropyl-5-methyl cyclohexane-carbonylamido propionic acid methyl ester, e.g., in a concentration of from about 0.001% to about 10%, particularly from about 0.01% to about 1% by weight (for example, not less than about 0.05% by weight, or not less than about 0.1% by weight).

It is further preferred for the preparations of the present invention to comprise one or more sunscreen agents and/or one or more antioxidants and/or one or more vitamins and/or one or more antiperspirants and/or one or more deodorants.

The cosmetic and dermatological preparations according to the present invention may be applied to the skin and/or the hair in sufficient quantities in the manner usual for cosmetics.

The cosmetic and dermatological preparations according to the present invention may further comprise one or more cosmetic auxiliaries which are customarily used in such preparations, e.g., preservatives, bactericides, perfumes, substances for preventing or increasing foaming, dyes, pigments which have a coloring action, thickeners, moisturizing and/or humectant substances, fats, oils, waxes or other customary constituents of a cosmetic or dermatological formulation, such as alcohols, polyols, polymers, foam stabilizers, electrolytes, organic solvents or silicone derivatives.

An additional content of conventional antioxidants is generally preferred. According to the invention, favorable antioxidants which may be used include all antioxidants which are customary or suitable for cosmetic and/or dermatological applications.

The amount of antioxidants (one or more compounds) in the preparations of the present invention is preferably from about 0.001% to about 30% by weight, particularly preferably from about 0.05% to about 20% by weight, in particular from about 0.1% to about 10% by weight, based on the total weight of the preparation.

If the cosmetic or dermatological preparation of the present invention is present as a solution or emulsion or dispersion, the following substances may, for example, be used as solvent:

water or aqueous solutions
oils such as triglycerides of capric or caprylic acid, but preferably sunflower oil;
fats, waxes and other natural and synthetic fatty bodies, preferably esters of fatty acids with alcohols of low carbon number, e.g., with isopropanol, propylene glycol or glycerol, or esters of fatty alcohols with alkanoic acids of low carbon number or with fatty acids;
alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

In particular mixtures of the above-mentioned solvents may be used. In the case of alcoholic solvents, water can be a further constituent.

As propellant for cosmetic and/or dermatological preparations of the present invention that are sprayable from aerosol containers the usual known volatile liquefied propellants, for example hydrocarbons (propane, butane, isobutane) are suitable which can be used alone or mixed with one another. Compressed air can also be used advantageously.

One skilled in the art will, of course, be familiar with the fact that there are non-toxic propellants, which would be suitable in principle for putting into practice the present invention in the form of aerosol preparations, but use thereof is not recommended—in particular fluorohydrocarbons and fluorochlorohydrocarbons (FCHCs)—due to their unacceptable effect on the environment or other accompanying circumstances.

Cosmetic preparations in accordance with the present invention may also be present as gels which comprise not only an effective amount of active ingredient according to the invention and conventionally used solvents therefor, preferably water, but also organic thickeners, for example gum arabic, xanthan gum, sodium alginate, cellulose derivatives, preferably methylcellulose, hydroxymethylcellulose, hydroxyethylcellulose, hydroxypropylcellulose, hydroxypropylmethylcellulose, or inorganic thickeners, for example aluminum silicates such as, for example, bentonites, or a mixture of polyethylene glycol and polyethylene glycol stearate or polyethylene glycol distearate. The gel may comprise the thickener in an amount of, for example, from about 0.1% to about 30% by weight, preferably from about 0.5% to about 15% by weight.

The preparation according to the present invention is preferably present in a form which is suitable for topical application. For example, the composition may be present in the form of a cream, a lotion, a gel, an ointment, a tincture, a skin oil, a milk, a balm, a tenside foam, an emulsion foam, a tenside gel, a bandage impregnated with the preparation, a cloth impregnated with the preparation, a textile impregnated with the preparation, a pad impregnated with the preparation, a spray, an aerosol, a roll-on, a stick, a soft solid, a powder or a powder spray.

Particularly advantageous preparations are furthermore obtained if one or more antioxidants are used as additives or active ingredients. Water-soluble antioxidants can be used very particularly advantageously, such as, for example, vitamins, e.g., ascorbic acid and derivatives thereof—in particular ascorbylpalmitate, Na and Mg ascorbylphosphate and ascorbylacetate—as well as rutinic acid and derivatives thereof in particular alpha-glucosylrutin, quercetin and isoquercetin, as well as isoflavones, in particular, genistein, genistin and daidzein.

Examples of particularly preferred antioxidants include furthermore vitamin E and derivatives thereof (in particular vitamin E acetate), vitamin A and derivatives thereof (in particular vitamin A palmitate), carnosine, butylated hydroxytoluol, butylated hydroxyanisol, ferulic acid, unsaturated fatty acids and derivatives thereof (e.g., gamma-linolenic acid, linolic acid and oleic acid), folic acid and derivatives thereof, beta-alanine, as well as carotenoids (in particular beta-carotene) and phytoene.

The concentration of the antioxidants (one or more compounds) in the preparations is preferably from about 0.001% to about 30% by weight, particularly preferably from about 0.05% to about 20% by weight, in particular from about 0.1% to about 10% by weight, based on the total weight of the preparation.

It may also be advantageous if the preparations according to the present invention comprise oil-soluble UVA filters and/or UVB filters in the lipid phase and/or water-soluble UVA filters and/or UVB filters in the aqueous phase.

Sunscreen containing formulations according to the present invention may advantageously comprise other substances which absorb UV radiation in the UVA and/or UVB range, the total amount of the filter substances being, for example, from about 0.1% to about 30% by weight, preferably from about 0.5% to about 10% by weight, in particular from about 1% to about 6% by weight, based on the total weight of the preparations, in order to provide cosmetic preparations that protect the skin from the entire range of ultraviolet radiation. They can also serve as sunscreen agents.

The following examples are intended to illustrate the present invention without restricting it. All quantities, proportions and percentages are based on the weight and the total quantity or on the total weight of the preparations unless stated otherwise.

| O/W Night Cream | % by weight |
|---|---|
| Glyceryl stearate citrate | 2 |
| Shea butter | 2 |
| Stearyl alcohol | 2 |
| Cetyl alcohol | 2 |
| Hydrogenated cocoglycerides | 2 |
| Caprylic/capric triglycerides | 2 |
| Ethylhexyl coconut fatty acid esters | 2 |
| Cyclomethicone | 3 |
| Dicaprylylether | 2 |
| Tocopherol | 0.1 |
| Folic acid | 0.1 |
| (1R,2S,5R)-2-Isopropyl-5-methyl-N-(2-(pyridin-2-yl)ethyl)-cyclohexane carboxamide | 0.3 |
| Retinyl palmitate | 0.1 |
| Phenoxyethanol | 0.6 |
| p-Hydroxybenzoic alkylester (Paraben) | 0.6 |
| Ethylhexylglycerin | 0.5 |
| Polyacrylic acid (Carbomer) | 0.1 |
| EDTA | 0.2 |
| Glycerin | 10 |
| water- and/or oil-soluble dyes | 0.05 |
| Fillers/Additives (SiO$_2$, BHT) | 0.2 |
| 2-Isopropyl-5-methyl-cyclohexanecarbonylamido-propionic acid methyl ester | 0.1 |
| Water | ad 100 |

| Skin Care Cream | % by weight | % by weight |
|---|---|---|
| Glyceryl stearate, self-emulsifying | 6 | 5 |
| Stearyl alcohol | 1 | 1 |
| Shea butter | 1 | 1 |
| C12-15 Alkylbenzoate | 3 | 3 |
| Caprylic/capric triglycerides | 2 | 2 |
| Mineral oil | 1 | 1 |
| Dicaprylyl carbonate | 3 | 3 |
| Ethylhexyl cyanodiphenylacrylate (Octocrylene) | 5 | 5 |
| Ethylhexyltriazone | 1 | 1 |
| Bis-ethylhexyloxyphenol-methoxy-phenyltriazine | 2 | 2 |
| Citric acid, sodium salt | 0.1 | 0.1 |
| Silymarin | | 0.05 |
| Phenoxyethanol | 0.6 | 0.6 |
| p-Hydroxybenzoic acid alkylester (Paraben) | 0.3 | 0.3 |
| Hexamidine diisethionate | 0.04 | 0.04 |
| 1,3-Dimethylol-5,5-dimethyl-hydantoin(DMDM Hydantoin) | 0.1 | 0.1 |
| EDTA | 0.2 | 0.2 |
| Vitamin B3 (Niacinamide) | 0.2 | |
| Ammonium acryloyldimethyltaurate/vinylpyrrolidone copolymers | 0.5 | 0.3 |
| Glycerin | 10 | 10 |
| (1R,2S,5R)-N-(4-Cyanomethyl-phenyl)-2-isopropyl-5-methylcyclohexane carboxamide | 1 | 0.3 |
| Additives (Distarch phosphate, SiO$_2$, BHT) | 1 | 1 |
| Perfume | q.s. | q.s. |
| Water | ad 100 | ad 100 |

| Sunscreen Cream | % by weight | % by weight |
|---|---|---|
| Glyceryl stearate | 3 | 3 |
| PEG-40 stearate | 1 | 1 |
| Cetearyl alcohol | 3 | 1 |
| Shea butter | 2 | 2 |
| C12-15 Alkylbenzoate | 2 | 2 |
| Cocoglycerides | — | 2 |
| Octyldodecanol | 3 | 3 |
| Beeswax | 1 | — |
| (1R,2S,5R)-N-(4-Cyanomethyl-phenyl)-2-isopropyl-5-methylcyclohexane carboxamide | 0.2 | — |
| Ethylhexyl methoxycinnamate | 5 | 5 |
| Phenylbenzimidazole sulfonic acid | 2 | 2 |
| Butylmethoxydibenzoylmethane | 2 | 2 |
| $TiO_2$ | 2 | 2 |
| Sodium ascorbylphosphate | 0.1 | 0.1 |
| Tocopheryl acetate | 1 | 1 |
| Methylpropanediol | 3 | 3 |
| (1R,2S,5R)-2-Isopropyl-5-methyl-N-(2-(pyridin-2-yl)ethyl)-cyclohexane carboxamide | 0.1 | 0.5 |
| p-Hydroxybenzoic acid alkylester (Paraben) | 0.2 | 0.2 |
| EDTA | 0.2 | 0.2 |
| Diazolidinyl urea | 0.1 | 0.1 |
| Carbomer | 0.1 | 0.1 |
| Carrageenan | 0.1 | 0.1 |
| Glycerin | 7 | 7 |
| Additives (BHT, Nylon-6) | 0.4 | 0.4 |
| Perfume | q.s. | q.s. |
| Water | ad 100 | ad 100 |

| O/W Cream for minimizing skin reddening | % by weight |
|---|---|
| Glyceryl stearate | 1 |
| Stearic acid | 3 |
| Stearyl alcohol | 2 |
| Cetyl alcohol | 2 |
| C12-15 Alkylbenzoate | 2 |
| Caprylic/capric triglycerides | 2 |
| Macadamia nut oil | 1 |
| Myristylmyristate | 2 |
| Dimethicone | 2 |
| Hydrogenated cocoglycerides | 1 |
| Ethylhexyl glycerin | 0.5 |
| Tocopheryl acetate | 1 |
| (1R,2S,5R)-N-(4-Cyanomethyl-phenyl)-2-isopropyl-5-methylcyclohexane carboxamide | 0.1 |
| Creatine | 0.1 |
| Ubiquinone (Q10) | 0.03 |
| Phenoxyethanol | 0.4 |
| p-Hydroxybenzoic acid alkylester (Paraben) | 0.3 |
| Iodopropinyl butylcarbamate | 0.02 |
| Cyclodextrin | 0.3 |
| Sodium citrate | 0.2 |
| Carbomer | 0.3 |
| Glycerin | 5 |
| Methylpropanediol | 3 |
| Additives ($SiO_2$, talc) | 0.5 |
| Perfume | q.s. |
| Water | ad 100 |

| After Sun Gel | % by weight |
|---|---|
| Cetyl alcohol | 2 |
| Shea butter | 1 |
| Caprylic/capric triglycerides | 2 |
| Octyldodecanol | 1 |
| Dicaprylyl carbonate | 5 |
| Dimethicone | 2 |
| Polydecene | 2 |
| Methyl palmitate | 3 |
| Licochalcone A | 0.02 |
| Sodium ascorbylphosphate | 0.05 |
| EDTA | 0.2 |
| (1R,2S,5R)-2-Isopropyl-5-methyl-N-(2-(pyridin-2-yl)ethyl)-cyclohexane carboxamide | 1.5 |
| Phenoxyethanol | 0.3 |
| p-Hydroxybenzoic acid alkylester (Paraben) | 0.4 |
| Cross-linked alkyl acrylate (alkyl acrylate crosspolymer) | 0.2 |
| Glycerin | 5 |
| Perfume | q.s. |
| Water | ad 100 |

| Skin-soothing After Shave Balm | % by weight | % by weight |
|---|---|---|
| Triceteareth-4-phosphate | 0.5 | 1.0 |
| Cyclomethicone | 2.0 | 2.0 |
| Octyldodecanol | — | 1.0 |
| Dicaprylyl carbonate | 3.0 | 3.0 |
| Methyl palmitatr | 2.0 | — |
| Carnitine | | 0.2 |
| Macadamia oil | 0.2 | 0.1 |
| (1R,2S,5R)-2-Isopropyl-5-methyl-N-(2-(pyridin-2-yl)ethyl)-cyclohexane carboxamide | 0.15 | |
| Ascorbylphosphate | | 0.2 |
| Arginine | 0.2 | |
| Phenoxyethanol | 0.5 | 0.5 |
| p-Hydroxybenzoic acid alkylester (Paraben) | 0.4 | 0.4 |
| Cross-linked alkyl acrylate (alkyl acrylate crosspolymer) | 0.3 | 0.3 |
| Distarch phosphate | 1.0 | 1.0 |
| Xanthan gum | 0.1 | 0.1 |
| (1R,2S,5R)-N-(4-Cyanomethyl-phenyl)-2-isopropyl-5-methylcyclohexane carboxamide | | 0.2 |
| Glycerin | 4.0 | 4.0 |
| Perfume | q.s. | q.s. |
| Water | ad 100 | ad 100 |

| (Self-foaming) skin soothing shaving foam | % by weight |
|---|---|
| Stearic acid | 6 |
| Laureth-23 | 4 |
| Stearyl alcohol | 0.5 |
| Soybean oil | 0.2 |
| Avocado oil | 0.1 |
| PEG-12 dimethicone | 0.8 |
| Hydroxypropylmethylcellulose | 0.4 |
| PEG-7M | 0.2 |
| Sodium ascorbyl phosphate | 0.05 |
| Additives (EDTA, BHT, Silica) | 0.2 |
| (1R,2S,5R)-2-Isopropyl-5-methyl-N-(2-(pyridin-2-yl)ethyl)-cyclohexane carboxamide | 0.1 |
| (1R,2S,5R)-N-(4-Cyanomethyl-phenyl)-2-isopropyl-5-methylcyclohexane carboxamide | 0.05 |
| p-Hydroxybenzoic acid alkylester (Paraben) | 0.4 |
| Glycerin | 3 |
| Propellant: Isobutane, Propane, Butane | qs |
| Perfume | q.s. |
| Water | ad 100 |

Packaging: aerosol container

| Deodorant Roll-On | | | | |
|---|---|---|---|---|
| Raw material (INCI) | % by weight | | | |
| Polyethylene glycol(21)stearylether | 3.000 | 3.000 | 3.000 | 1.500 |
| Polyethylene glycol(2)stearylether | 2.000 | 2.000 | 2.500 | 3.000 |
| Polypropylene glycol(15)stearylether | 2.000 | 3.000 | 3.000 | — |
| Coconut fatty acid-2-ethylhexyl ester | — | — | 1.000 | — |
| EDTA | 0.200 | 0.200 | 0.200 | 0.200 |
| Avocado oil | 0.100 | 0.100 | 0.100 | 0.100 |
| Aluminum chlorohydrate | 8.000 | 12.000 | 10.000 | 5.000 |
| Perfume, antioxidants (BHT, ascorbyl palmitate) | q.s. | q.s. | q.s. | q.s. |
| (1R,2S,5R)-2-Isopropyl-5-methyl-N-(2-(pyridin-2-yl)ethyl)-cyclohexane carboxamide | 0.1 | — | 0.1 | — |
| (1R,2S,5R)-N-(4-Cyano-methyl-phenyl)-2-isopropyl-5-methylcyclohexane carboxamide | — | 0.2 | 0.05 | 0.1 |
| Water, ad | 100.000 | 100.000 | 100.000 | 100.00 |

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A method of reducing skin reddening, wherein the method comprises applying to skin of a subject in need thereof and in an amount which is effective for reducing skin reddening, a topical cosmetic or dermatological preparation which comprises at least 0.1% by weight, based on a total weight of the preparation, of at least one of (i) (1R,2S,5R)-2-isopropyl-5-methyl-N-(2-(pyridin-2-yl)ethyl)-cyclohexane carboxamide and (ii) (1R,2S,5R)-N-(4-cyanomethyl-phenyl)-2-isopropyl-5-methylcyclohexane carboxamide.

2. The method of claim 1, wherein the preparation comprises at least (i).

3. The method of claim 1, wherein the preparation comprises at least (ii).

4. The method of claim 1, wherein the preparation comprises both (i) and (ii).

5. The method of claim 1, wherein the preparation further comprises (iii) 2-isopropyl-5-methylcyclohexane carbonylamido propionic acid methyl ester.

6. The method of claim 1, wherein the preparation comprises not more than 1% by weight of the at least one of (i) and (ii).

7. The method of claim 5, wherein the preparation comprises at least 0.05% by weight of (iii), based on a total weight of the preparation.

8. The method of claim 7, wherein the preparation comprises from about 0.1% to about 1% by weight of (iii), based on a total weight of the preparation.

9. The method of claim 1, wherein the preparation is present as an emulsion.

10. The method of claim 1, wherein the preparation further comprises at least one sunscreen agent.

11. A method of reducing skin reddening after shaving, wherein the method comprises applying to shaved skin of a subject in need thereof and in an amount which is effective for reducing skin reddening, a topical cosmetic or dermatological preparation which comprises at least 0.1% by weight, based on a total weight of the preparation, of at least one of (i) (1R,2S,5R)-2-isopropyl-5-methyl-N-(2-(pyridin-2-yl)ethyl)-cyclohexane carboxamide and (ii) (1R,2S ,5R)-N-(4-cyanomethyl-phenyl)-2-isopropyl-5-methylcyclohexane carboxamide.

12. The method of claim 11, wherein the preparation comprises at least (i).

13. The method of claim 11, wherein the preparation comprises at least (ii).

14. The method of claim 11, wherein the preparation comprises both (i) and (ii).

15. The method of claim 11, wherein the preparation further comprises (iii) 2-sopropyl-5-methylcyclohexane carbonylamido propionic acid methyl ester.

16. The method of claim 11, wherein the preparation comprises not more than 1% by weight of the at least one of (i) and (ii).

17. The method of claim 15, wherein the preparation comprises at least 0.05% by weight of (iii), based on a total weight of the preparation.

18. The method of claim 17, wherein the preparation comprises from about 0.1% to about 1% by weight of (iii), based on a total weight of the preparation.

19. The method of claim 11, wherein the preparation is present as an after shave balm.

20. The method of claim 11, wherein the preparation is present as a shaving foam.

* * * * *